US011657901B2

(12) United States Patent
Abdolahi et al.

(10) Patent No.: US 11,657,901 B2
(45) Date of Patent: May 23, 2023

(54) SYSTEM AND METHOD FOR PREDICTION-MODEL-BASED DISPLAY OF DISTRIBUTIONS OF HEALTH OUTCOME INFORMATION FOR PATIENT POPULATIONS IN GEOGRAPHICAL AREAS

(71) Applicant: KONINKLIJKE PHILIPS N.V., Eindhoven (NL)

(72) Inventors: Amir Abdolahi, Waltham, MA (US); Cecilia Meijer, Cambridge, MA (US); Eran Simhon, Boston, MA (US); Gertjan Laurens Schuurkamp, Utrecht (NL); Reza Sharifi Sedeh, Malden, MA (US); Jordan Lento, Alpharetta, GA (US)

(73) Assignee: Koninklijke Philips N.V., Eindhoven (NL)

( * ) Notice: Subject to any disclaimer, the term of this patent is extended or adjusted under 35 U.S.C. 154(b) by 842 days.

(21) Appl. No.: 16/199,701

(22) Filed: Nov. 26, 2018

(65) Prior Publication Data

US 2019/0213302 A1 Jul. 11, 2019

Related U.S. Application Data

(60) Provisional application No. 62/613,817, filed on Jan. 5, 2018.

(51) Int. Cl.
| | | |
|---|---|---|
| G16B 45/00 | (2019.01) | |
| G16H 50/30 | (2018.01) | |
| G16H 50/70 | (2018.01) | |
| G16B 40/00 | (2019.01) | |
| G16H 50/80 | (2018.01) | |

(52) U.S. Cl.
CPC ............. *G16B 45/00* (2019.02); *G16B 40/00* (2019.02); *G16H 50/30* (2018.01); *G16H 50/70* (2018.01); *G16H 50/80* (2018.01)

(58) Field of Classification Search
None
See application file for complete search history.

(56) References Cited

U.S. PATENT DOCUMENTS

| | | |
|---|---|---|
| 2010/0082362 A1 | 4/2010 | Carroll |
| 2017/0091397 A1 | 3/2017 | Shah |

FOREIGN PATENT DOCUMENTS

WO    2014028639 A2    2/2014

OTHER PUBLICATIONS

Shaman, Jeffrey, et al. "Real-time influenza forecasts during the 2012-2013 season." Nature communications 4.1 (2013): 1-10.*
Carroll, Lauren N., et al. "Visualization and analytics tools for infectious disease epidemiology: a systematic review." Journal of biomedical informatics 51 (2014): 287-298.*
Barrat, Alain, et al. "Measuring contact patterns with wearable sensors: methods, data characteristics and applications to data-driven simulations of infectious diseases." Clinical Microbiology and Infection 20.1 (2014): 10-16.*
Thomas C. Ricketts et al., "Geography and Disparity in Health", Cecil G. Sheps Center for Health Services Research University of North Carolina at Chapel Hill, Mar. 2002.

* cited by examiner

*Primary Examiner* — G Steven Vanni

(57) ABSTRACT

The present system is configured to display distributions of predicted health outcome information for patient populations in geographical areas. The system is configured to obtain demographic, social (e.g., including environmental), and prior health outcome information for a patient population in a geographical area. The system is configured to train a prediction model based on the demographic, social, and prior health outcome information, which outputs weighted features of the demographic and social information that are predictive of health outcomes for the patient population. The system is configured to cause display of a distribution of predicted health outcome information for the patient population in the geographical area based on the weighted features.

11 Claims, 11 Drawing Sheets

SYSTEM AND METHOD FOR PREDICTION-MODEL-BASED DISPLAY OF DISTRIBUTIONS OF HEALTH OUTCOME INFORMATION FOR PATIENT POPULATIONS IN GEOGRAPHICAL AREAS

CROSS-REFERENCE TO PRIOR APPLICATIONS

This application claims the benefit of U.S. Provisional application No. 62/613,817, filed on 5 Jan. 2018. This application is hereby incorporated by reference herein.

BACKGROUND

1. Field

The present disclosure pertains to a system and method for displaying distributions of predicted health outcome information for patient populations in geographical areas.

2. Description of the Related Art

Hospital networks often serve large geographical areas having varying density and population demographics. Typical computing systems used by hospital networks can map addresses of patients and/or hospital network resources such as hospitals, clinics, doctors, etc. Typical computing systems also electronically record patient information in electronic medical records.

SUMMARY

Accordingly, one or more aspects of the present disclosure relate to a system configured to display distributions of predicted health outcome information for patient populations in geographical areas. The system comprises one or more hardware processors configured by machine readable instructions, and/or other components. The system is configured to obtain demographic, social, and prior health outcome information for a patient population in a geographical area. The demographic and social information is related to one or more of economics, neighborhood environments, education, health insurance coverage, or social interactions of the patient population. The prior health outcome information indicates one or more of medical conditions experienced by the patient population, treatments received by the patient population, or results of the treatments on the medical conditions for the patient population. The system is configured to cause a prediction model to be trained based on the demographic, social, and prior health outcome information, by providing the demographic, social, and prior health outcome information, as input to the prediction model. The system is configured to cause the prediction model to output weighted features of the demographic and social information that are predictive of health outcomes for the patient population. The system is configured to cause display of a distribution of predicted health outcome information for the patient population in the geographical area based on the weighted features. The distribution of predicted health outcome information comprises one or more fields in one or more views of a graphical user interface indicating information related to one or more of: criteria received from a user used to define the patient population, a number of patients in the patient population, an indication of relative influence of individual weighted features on the distribution, or health outcome risk indicators for medical conditions in specific regions of the geographical area.

Another aspect of the present disclosure relates to a method for displaying distributions of predicted health outcome information for patient populations in geographical areas with a display system. The system comprises one or more hardware processors configured by machine readable instructions and/or other components. The method comprises obtaining demographic, social, and prior health outcome information for a patient population in a geographical area. The demographic and social information is related to one or more of economics, neighborhood environments, education, health insurance coverage, or social interactions of the patient population. The prior health outcome information indicates one or more of medical conditions experienced by the patient population, treatments received by the patient population, or results of the treatments on the medical conditions for the patient population. The method comprises causing a prediction model to be trained based on the demographic, social, and prior health outcome information, by providing the demographic, social, and prior health outcome information, as input to the prediction model. The method comprises causing the prediction model to output weighted features of the demographic and social information that are predictive of health outcomes for the patient population. The method comprises causing display of a distribution of predicted health outcome information for the patient population in the geographical area based on the weighted features. The distribution of predicted health outcome information comprises one or more fields in one or more views of a graphical user interface indicating information related to one or more of: criteria received from a user used to define the patient population, a number of patients in the patient population, an indication of relative influence of individual weighted features on the distribution, or health outcome risk indicators for medical conditions in specific regions of the geographical area.

Still another aspect of present disclosure relates to a system for displaying distributions of predicted health outcome information for patient populations in geographical areas. The system comprises means for obtaining demographic, social, and prior health outcome information for a patient population in a geographical area. The demographic and social information is related to one or more of economics, neighborhood environments, education, health insurance coverage, or social interactions of the patient population. The prior health outcome information indicates one or more of medical conditions experienced by the patient population, treatments received by the patient population, or results of the treatments on the medical conditions for the patient population. The system comprises means for causing a prediction model to be trained based on the demographic, social, and prior health outcome information, by providing the demographic, social, and prior health outcome information, as input to the prediction model. The system comprises means for causing the prediction model to output weighted features of the demographic and social information that are predictive of health outcomes for the patient population. The system comprises means for causing display of a distribution of predicted health outcome information for the patient population in the geographical area based on the weighted features. The distribution of predicted health outcome information comprises one or more fields in one or more views of a graphical user interface indicating information related to one or more of: criteria received from a user used to define the patient population, a number of patients in the patient population, an indication of relative influence of individual weighted features on the distribution, or health outcome risk indicators for medical conditions in specific regions of the geographical area.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
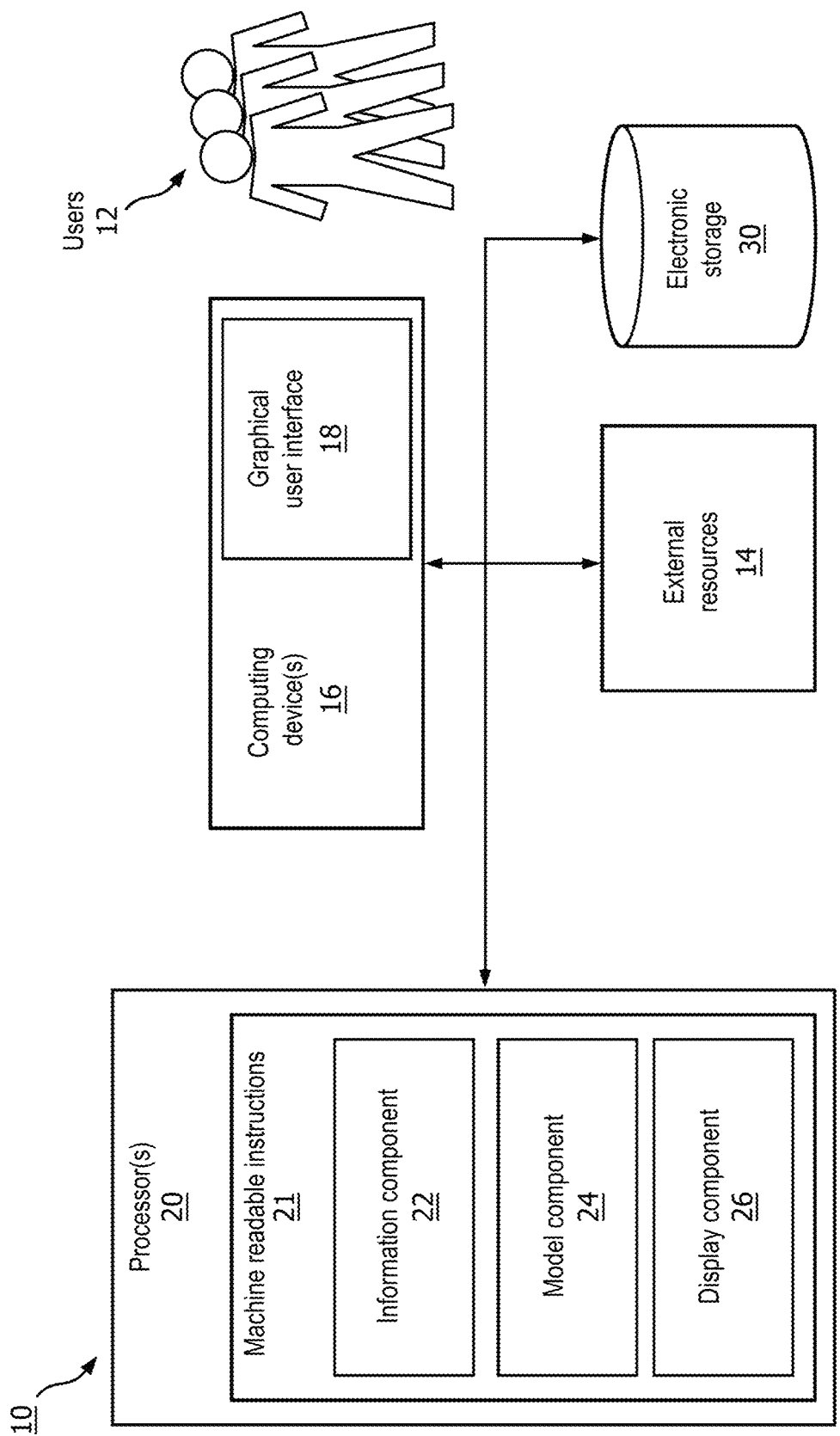
FIG. 1 illustrates a system configured to display distributions of predicted health outcome information for patient populations in geographical areas, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to display distributions of predicted health outcome information for patient populations in geographical areas. In some embodiments, system 10 displays the distributions of predicted heath outcome information for patient populations to one or more users 12. In some embodiments, users 12 are or are part of a medical care provider system and/or include other users. In some embodiments, the medical care provider system is or includes a hospital system such as an accountable care organization (ACO), and/or other medical care provider systems.

Medical care provider system resources such as hospitals, clinics, outpatient facilities, physician practices, nurses, care management teams, etc., tend to be located in and around the main hospitals of the medical care provider systems. Locating resources in this way often does not account for patient access and/or specialty treatment needs. Medical care provider systems are often aware of the medical conditions experienced by their patients, but rarely consider the demographic and social features (e.g., determinants such as environment, availability of healthy living activities, access to care, etc.) of a population when allocating resources.

System 10 is a systematic tool that medical care provider systems and/or other users may use to visualize where patients with specific conditions are located in order to strategically focus resources and/or expand the necessary staff and/or facilities into a given region. Based on social features, for example, some geographical areas (e.g., zip codes) may benefit more from telemedicine services, while other geographical areas may need a physical clinic to treat one or more medical conditions experienced by a number of patients in that region. System 10 integrates demographic and social information for a patient population from a geographical area (e.g., obtained from public databases, etc. as described below) with prior health outcome information (e.g., as described below) from medical care provider systems to predict health outcomes for patient populations and display distributions of predicted health outcome information across a geographical region.

Advantageously, system 10 models and displays the predicted health outcome information for a patient population relative to the geographical area (e.g., by zip code, etc.) The model and display are customizable based on targeted demographic, social, and/or prior health outcome features so that a medical care provider system can model and visualize predicted characteristics of a patient population in the geographical area and strategically align their facilities and/or other resources (e.g. personnel) in corresponding areas. This may limit under and/or over-utilization of the resources of the medical care provider system and/or have other advantages. For example, if there is a large heart failure population in a geographical area corresponding to a specific postal (e.g., zip) code and/or cluster of postal codes, a specialty clinic may be placed in that area to promote better management of heart failure symptoms and/or reduce the number of unplanned preventable hospitalizations at a larger city hospital. As other examples, strategic alignment of resources may increase the availability of and/or adherence to prescription medications (e.g., because there are more pharmacies and/or treatment facilities closer to patients in need), telehealth services may be offered to more rural areas that do not have easy access to public transportation, and/or a medical care provider system may choose to offer incentives to join a gym in areas with little green space based on the model and/or display by system 10. These examples are not intended to be limiting.

In some embodiments, system 10 comprises one or more of external resources 14, computing devices 16, processors 20, electronic storage 30, and/or other components.

External resources 14 include sources of information and/or other resources. For example, external resources 14 may include sources of demographic information, social information, prior health outcome information, and/or other information. This information may be related to a patient population in a given geographical area, a neighborhood environment of that geographical area, and/or other patient populations. In some embodiments, the demographic information is related to gender, ethnicity, age, postal address (e.g., zip code), language spoken, number of children, health literacy, literacy level in general, and/or other demographic information. In some embodiments, the social information is related to one or more of economics, neighborhood environments, education, health insurance coverage, social interactions of the patient population, and/or other information related to a patient population. For example, the social information may include and/or be related to property values, crime rates, economic prosperity measures such as income level, education level, access to education, local public school ratings, a level of social interaction, distances to medical facilities, access to public transportation, access to parks, household income, proportion of subsidized housing in a particular zip code, and/or other information associated with patients of a patient population. In some embodiments, the social information includes neighborhood environment information such as information related to pollution levels/air quality in the neighborhood, and/or other environmental information. In some embodiments, the demographic and/or social information may be and/or include social determinants of health (e.g., as described in the Health People 2020 Initiative) and/or include other information.

In some embodiments, the prior health outcome information indicates one or more of medical conditions experienced by the patient population, treatments received by the patient population, results of the treatments on the medical conditions for the patient population, and/or other information. For example, in some embodiments, the information from external resources 14 is related to one or more physiological conditions of the patients in the population and/or other information. In some embodiments, the information from external resources 14 includes information from electronic medical records associated with patients of the patient population. Such information may include information related to patient demographics, vital signs information indicating vital signs associated with patients, medical condition information indicating medical conditions experienced by patients, treatment information indicating treatments received by patients, outcome information indicating corresponding health outcomes for patients, and/or other health information.

In some embodiments, the demographic, social, and/or prior health outcome information includes information obtained via a server and/or other computing systems included in external resources 14 that are associated with a caregiver, a care facility, a medical care provider system, a government entity, and/or other external computing systems. In some embodiments, external resources 14 include sources of demographic, social, and/or prior health outcome information such as databases (e.g., of population census information, postal code information, crime information, property value information, etc.), websites (e.g., social interaction websites), etc.; external entities participating with system 10 (e.g., a medical records system of a health care provider that stores medical history information for populations of patients), one or more servers outside of system 10 (e.g., a server that stores information related to a daily schedule of activities/interactions for patients in the patient population), one or more computer systems associated with a care provider (e.g., a doctor's office, hospital, etc.) that communicate information to or from system 10 electronically (e.g., via email, text, etc.), and/or other sources of information. In some embodiments, the prior heath outcome information, for example, includes information obtained via one or more sensors (e.g., also included in external resources 14) monitoring patients in the patient population, other sensor information related to the physiological conditions of patients, and/or other sensor information. For example, external resources 14 may include one or more wearable devices configured to track physiological information associated with patients, a scale or other devices used in the home to track physiological characteristics of patients, sensors associated with care facilities that provide care to patients, and/or other sensors.

In some embodiments, external resources 14 include components that facilitate communication of information such as a network (e.g., the internet), electronic storage, equipment related to Wi-Fi technology, equipment related to Bluetooth® technology, data entry devices, sensors, scanners, and/or other resources. External resources 14 may be configured to communicate with computing devices 16, processor 20, electronic storage 30, and/or other components of system 10 via wired and/or wireless connections, via a network (e.g., a local area network and/or the internet), via cellular technology, via Wi-Fi technology, and/or via other resources. In some embodiments, some or all of the functionality attributed herein to external resources 14 may be provided by resources included in system 10.

Computing devices 16 are configured to provide interfaces between users 12 (e.g., users associated with medical care provider systems, hospital systems, ACO's and other systems; users associated with medical care facilities; individual administrators, doctors, nurses, staff members, technicians, etc.), and/or other users, and system 10. In some embodiments, individual computing devices 16 are and/or are included in desktop computers, laptop computers, tablet computers, smartphones, and/or other computing devices associated with individual users 12, and/or other users. In some embodiments, individual computing devices 16 are, and/or are included in computing equipment used by medical care provider systems, in hospitals, doctor's offices, and/or other medical facilities; data entry equipment; and/or other devices. Computing devices 16 are configured to provide information to and/or receive information from users 12, and/or other users. For example, computing devices 16 are configured to present a graphical user interface 18 to users 12 to display the distributions of predicted health outcome information (e.g., as described below), facilitate entry and/or selection of population criteria (e.g., as described below), and/or for other purposes. In some embodiments, graphical user interface 18 includes a plurality of separate interfaces associated with computing devices 16, processors 20, and/or other components of system 10; multiple views and/or fields configured to convey information to and/or receive information from users 12 (e.g., as described below), and/or other users; and/or other interfaces.

In some embodiments, computing devices 16 are configured to provide graphical user interface 18, processing capabilities, databases, electronic storage, and/or other resources to system 10. As such, computing devices 16 may include processors 20, electronic storage 30, external resources 14, and/or other components of system 10. In some embodiments, computing devices 16 are connected to a network (e.g., the internet). In some embodiments, computing devices 16 do not include processors 20, electronic storage 30, external resources 14, and/or other components of system 10, but instead communicate with these components via the network. The connection to the network may be wireless or wired. For example, one or more processors 20 may be located in a remote server and may wirelessly cause display of graphical user interface 18 to a user 12 on a computing device 16 associated with a medical care provider system, and/or to a user 12 on a computing device 16 associated with user 12. As described above, in some embodiments, an individual computing device 16 is a laptop, a personal computer, a smartphone, a tablet computer, and/or other computing devices. Examples of interface devices suitable for inclusion in an individual computing device 16 include a touch screen, a keypad, touch sensitive and/or physical buttons, switches, a keyboard, knobs, levers, a display, speakers, a microphone, an indicator light, an audible alarm, a printer, and/or other interface devices. The present disclosure also contemplates that an individual computing device 16 includes a removable storage interface. In this example, information may be loaded into a computing device 16 from removable storage (e.g., a smart card, a flash drive, a removable disk) that enables users 12, and/or other users to customize the implementation of computing devices 16 and/or system 10. Other exemplary input devices and techniques adapted for use with computing devices 16 include, but are not limited to, an RS-232 port, RF link, an IR link, a modem (telephone, cable, etc.) and/or other devices.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., a server), or processor 20 may represent processing functionality of a plurality of devices operating in coordination (e.g., one or more servers, devices that are part of external resources 14, computing devices 16, electronic storage 30, and/or other devices.)

In some embodiments, processor 20, external resources 14, computing devices 16, electronic storage 30, and/or other components may be operatively linked via one or more electronic communication links. For example, such electronic communication links may be established, at least in part, via a network such as the Internet, and/or other networks. It will be appreciated that this is not intended to be limiting, and that the scope of this disclosure includes embodiments in which these components may be operatively linked via some other communication media. In some embodiments, processor 20 is configured to communicate with external resources 14, computing devices 16, electronic storage 30, and/or other components according to a client/server architecture, a peer-to-peer architecture, and/or other architectures.

As shown in FIG. 1, processor 20 is configured via machine-readable instructions 21 to execute one or more computer program components. The one or more computer program components comprise one or more of an information component 22, a model component 24, a display component 26, and/or other components. Processor 20 may be configured to execute components 22, 24, and/or 26 by software; hardware; firmware; some combination of software, hardware, and/or firmware; and/or other mechanisms for configuring processing capabilities on processor 20.

It should be appreciated that although components 22, 24, and 26 are illustrated in FIG. 1 as being co-located within a single processing unit, in embodiments in which processor 20 comprises multiple processing units, one or more of components 22, 24, and/or 26 may be located remotely from the other components. The description of the functionality provided by the different components 22, 24, and/or 26 described below is for illustrative purposes, and is not intended to be limiting, as any of components 22, 24, and/or 26 may provide more or less functionality than is described. For example, one or more of components 22, 24, and/or 26 may be eliminated, and some or all of its functionality may be provided by other components 22, 24, and/or 26. As another example, processor 20 may be configured to execute one or more additional components that may perform some or all of the functionality attributed below to one of components 22, 24, and/or 26.

Information component 22 is configured to obtain demographic, social, and prior health outcome information for a patient population in a geographical area. As described above, the demographic and social information is related to economics of the patient population, neighborhood environments of the patient population, education of the patient population, health insurance coverage of the patient population, social interactions of the patient population, where patients live (e.g., addresses, postal codes, etc.) and/or other information related to the patient population. The prior health outcome information indicates medical conditions experienced by the patient population, treatments received by the patient population, results of the treatments on the medical conditions for the patient population, and/or other prior health outcome information for the patient population. In some embodiments, information component 22 is configured to obtain the demographic, social, and prior health outcome information electronically from external resources 14, computing devices 16, electronic storage 30, and/or other sources of information.

In some embodiments, obtaining the demographic, social, and prior health outcome information electronically from external resources 14, computing devices 16, electronic storage 30, and/or other sources of information comprises querying one more databases and/or servers; uploading information and/or downloading information, facilitating user input (e.g., criteria used to define a target patient population, geographical area, etc. input via computing devices 16), sending and/or receiving emails, sending and/or receiving text messages, and/or sending and/or receiving other communications, and/or other obtaining operations. In some embodiments, information component 22 is configured to aggregate information from various sources (e.g., one or more of the external resources 14 described above, computing devices 16, electronic storage 30, etc.), arrange the information in one or more electronic databases (e.g., electronic storage 30 and/or other electronic databases), normalize the information based on one or more features of the demographic, social, and prior health outcome information (e.g., population size and/or other features), and/or perform other operations.

In some embodiments, the demographic, social, and prior health outcome information comprises demographic, social, and prior health outcome features and/or other information. By way of a non-limiting example, in some embodiments, the demographic features may comprise features (e.g., gender, ethnicity, age, postal address, etc.) associated with demographics of patients in the patient population. The prior health outcome features may comprise medical condition features (e.g., a disease type, disease severity, symptoms, behaviors, heart rate, body mass index, temperature, respiration rate, number of comorbidities, prior hospitalizations, etc.) associated with medical conditions experienced by patients, treatment features (e.g., length of treatment, length of stay in a medical facility, type and quantity of medications, interventions, specialty services, etc.) associated with treatments received by patients, outcome features (e.g., discharge date, prognosis, readmission date, readmission risk, risk of morbidity and mortality, cost, etc.) associated with health outcomes for patients, and/or other features. The social features may comprise features (e.g., economic prosperity, education level, health literacy, property value, local crime rate, income level, local public school ratings, health insurance coverage, a level of social interaction, distances to medical facilities, access to public transportation, distance to parks, etc.) associated with the social behavior of patients, and/or other feature related information. It should be noted that the example features described above are not intended to be limiting. An uncountable number of possible features exist and those listed above are a small subset of examples.

Model component 24 is configured to cause one or more prediction models to be trained. Model component 24 is configured to cause the one or more prediction models to be trained based on the demographic, social, and prior health outcome information, and/or other information. Model component 24 is configured to cause the one or more prediction models to be trained based on the demographic, social, and prior health outcome information, patient population criteria entered and/or selected by a user 12, and/or other information, by providing the demographic, social, and prior health outcome information, patient population criteria, and/or other information (e.g., on the zip code level and/or on a broader level) as input to the prediction model. The prediction models may be and/or include a regression model, machine learning algorithms, one or more neural networks (e.g., recurrent neural networks, multiresolution recurrent neural networks, etc.), generalized linear models, Hidden Markov Models, rules based and/or probabilistic models, and/or other prediction models. In some embodiments, the one or more prediction models may be similar to and/or the same as the prediction model(s) described in U.S. Patent Application No. 62/587,921, titled "An Adjustable Socio-Economic Indexing System", which is hereby incorporated by reference in its entirety.

Model component 24 is configured such that the one or more prediction models are based on features of the demographic, social, and prior health outcome information such as age, ethnicity, language, marital status, social economic features derived based on patient postal codes and/or addresses using public data sets (e.g., on servers and/or in other databases included in external resources 14), and/or other features. In some embodiments, model component 24 is configured such that a weight and/or importance of each feature is determined by machine learning algorithms and/or other methods. The one or more prediction models predict health outcomes and/or a combination of health outcomes specified by users 12 (e.g., criteria that defines the patient population entered and/or selected via computing devices 16). For example, responsive to entry and/or selection of patient population criteria from one or more users 12, the one or more prediction models may output information that indicates specific regions (e.g., zip codes) of the geographical area with the highest occurrences of a target medical condition (e.g., diabetes). As another example, the one or more prediction models may output information that indicates a list of postal codes sorted by population size and prevalence of one or more target chronic conditions. Model component 24 is configured to cause the one or more prediction models to output one or more of the weighted features of the demographic and social information that are predictive of corresponding health outcomes for the patient population.

In some embodiments, model component 24 is configured such that the machine learning algorithms output one or more regression models which predict the health outcomes based on the weighted features, information used to inform users on market expansion opportunities and guide resource allocation (e.g. staffing, building new clinics where needed, etc.), and/or other information. In some embodiments, model component 24 is configured such that the one or more prediction models (e.g., the one or more machine learning algorithms) may be and/or include one or more neural networks that are trained and utilized for generating outputs (as described herein). As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function which combines the values of all its inputs together. In some embodiments, each connection (or the neutral unit itself) may have a threshold function such that the signal must surpass the threshold before it is allowed to propagate to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free-flowing, with connections interacting in a more chaotic and complex fashion.

Figure 2:
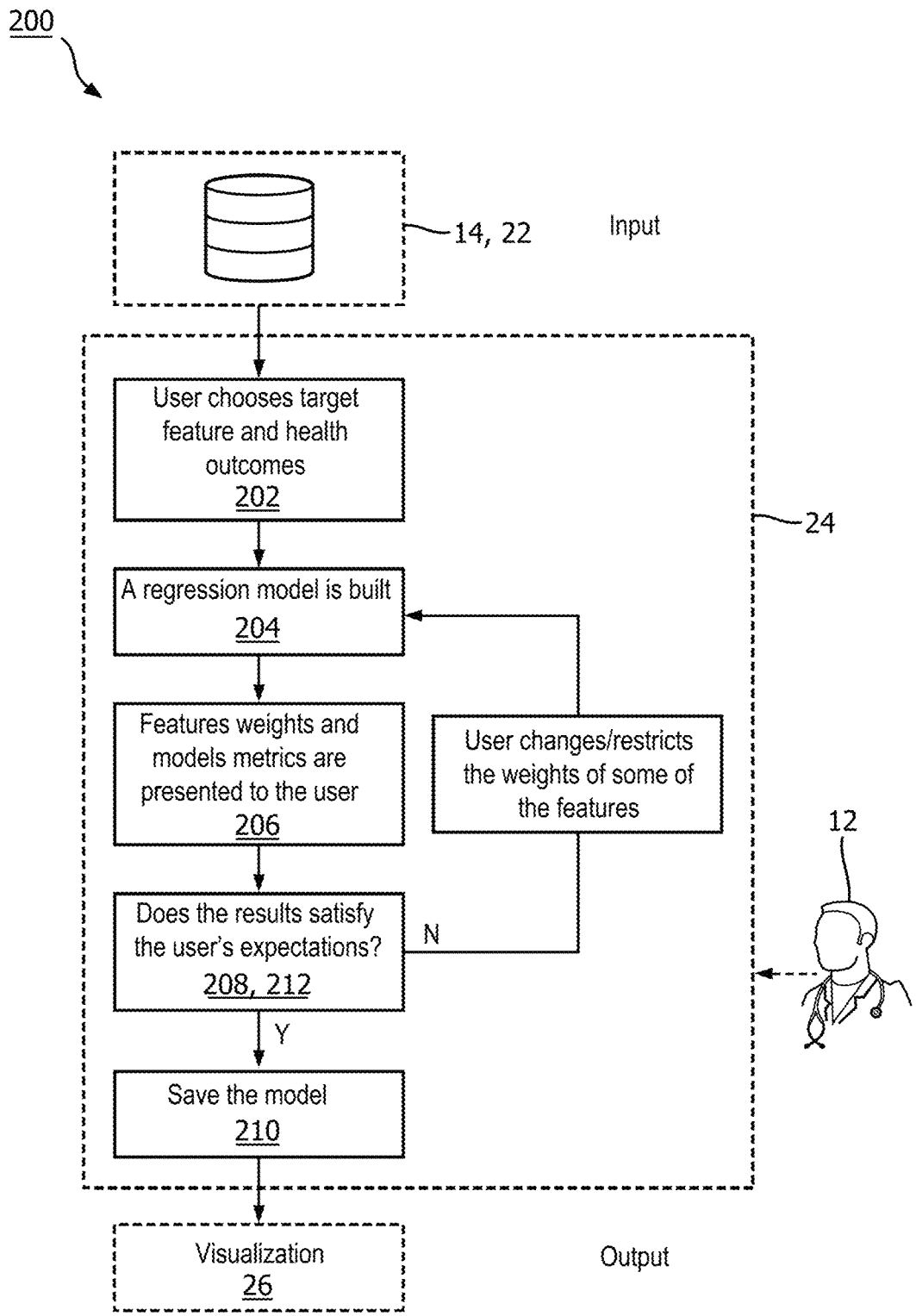
FIG. 2 is a schematic illustration of operations performed by a model component of the system, in accordance with one or more embodiments.

By way of a non-limiting example, FIG. 2 is a schematic illustration of operations performed by model component 24. As shown in FIG. 2, model component 24 receives the demographic, social, and prior health outcome information for a patient population in a geographical area from information component 22 (e.g., via one or more databases and/or other sources of information included in external resources 14). Model component 24 also receives 202 entry and/or selection of criteria from user 12 that defines the patient population and/or the geographical region, and/or limits the modeled patient population in other ways. Model component 24 then builds and/or trains 204 the model and outputs 206 feature weights and/or other model metrics. In some embodiments, responsive to the model satisfying 208 the expectations of user 12, model component 24 saves 210 the model (e.g., in electronic storage 30 shown in FIG. 1) and visualization operations performed by display component 26 commence. In some embodiments, responsive to the model not satisfying 212 the expectations of user 12, model component 24 then facilitates re-entry and/or adjustment 214 of the criteria used to limit the modeled patient population, and the model building and training operations 204 repeat. As noted above, these modelling operations and/or similar operations are described in U.S. Patent Application No. 62/587,921.

Returning to FIG. 1, display component 26 is configured to cause display of a distribution of predicted health outcome information for a patient population in a geographical area. Display component 26 is configured to cause the display of the distribution of predicted health outcome information for a patient population in a geographical area based on the weighted features and/or other output from the one or more prediction models. The distribution of predicted health outcome information comprises one or more fields in one or more views of graphical user interface 18 (of computing devices 16) indicating information related to one or more of criteria received from a user 12 used to define the patient population, a number of patients in the patient population, an indication of relative influence of individual weighted features on the distribution, health outcome risk indicators for medical conditions in specific regions (e.g., zip codes and/or other postal codes) of the geographical area, and/or other information. In some embodiments, the display comprises graphical, textual, or other representations. In some embodiments, the display comprises provision of one or more textual and/or graphical fields in various views of graphical user interface 18 and/or other displays.

In some embodiments, display component 26 is configured to communicate with user interface 18 to facilitate entry and/or selection of the criteria used to define and/or adjust the patient population. In some embodiments, display component 26 is configured to re-display a distribution based on adjusted criteria. In some embodiments, display component 26 is configured to communicate with user interface 18 to facilitate expansion and contraction, pop up, and/or other display of one or more menus, fields, and/or other objects within or adjacent to one or more of the other fields. In some embodiments, display component 26 causes such displays responsive to pointing, clicking, and/or hovering over a specific portion of the display with a pointer and/or other indicator by a user. In some embodiments, the expanded fields, the pop-up fields, additional menu items, and/or other objects display additional complimentary and/or corresponding (e.g., to a specific zip code) information to the user (e.g., user 12).

Figure 3:
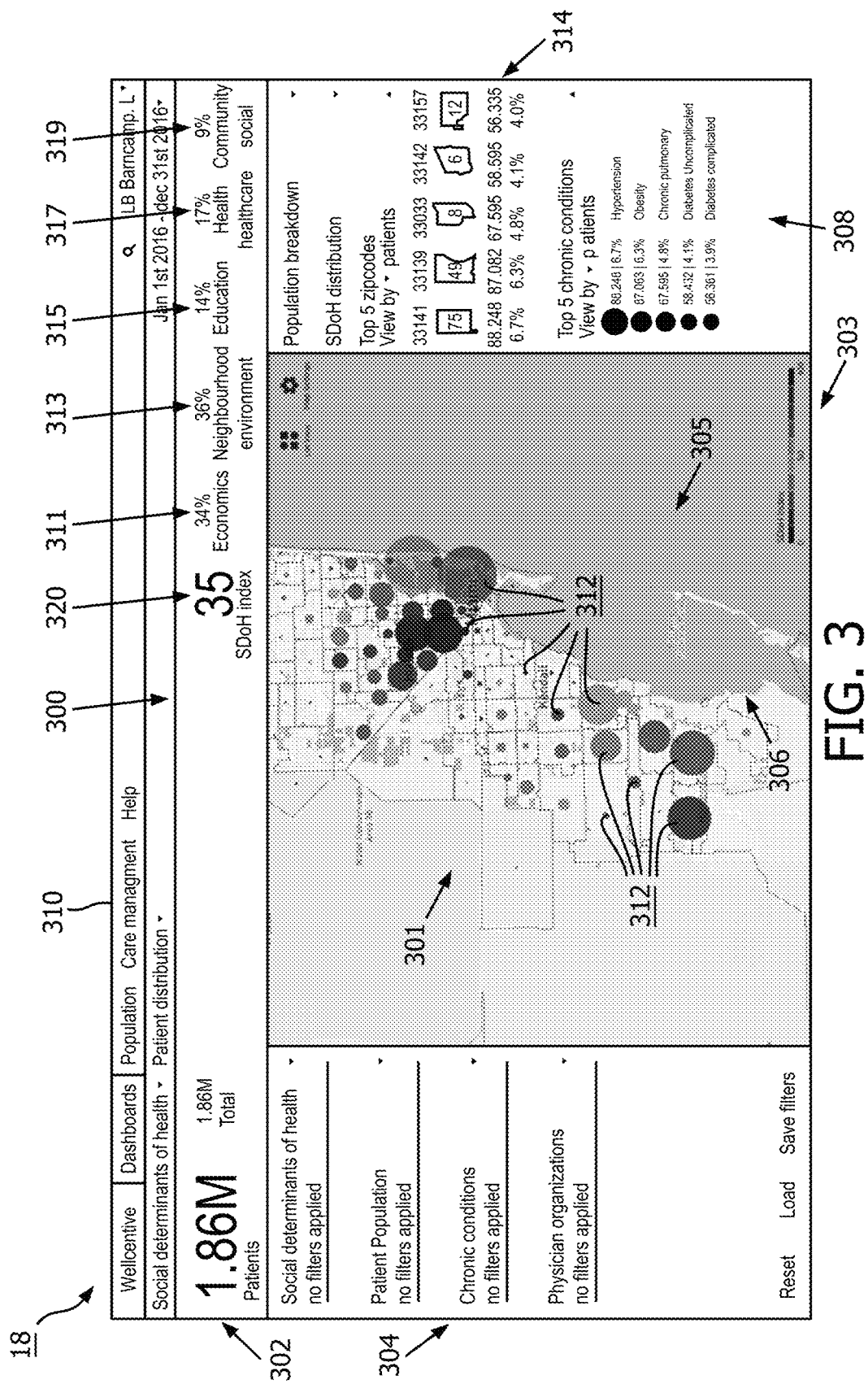
FIG. 3 illustrates a distribution of predicted health outcome information for a patient population in a geographical area, in accordance with one or more embodiments.

For example, FIG. 3 illustrates a distribution 301 of predicted health outcome information 303 for a patient population in a geographical area 305 (e.g., greater Miami). In some embodiments, distribution 301 comprises a map of geographical area 305. In FIG. 3, distribution 301 comprises zip codes (e.g., the top five zip codes) sorted by a feature (e.g. population size), and chronic conditions (e.g., the top five chronic conditions) shown by zip code shown on the map of the greater Miami geographical area. FIG. 3 illustrates a plurality of fields 300, 302, 304, 306, 308, in a view 310 of graphical user interface 18 (of computing devices 16 shown in FIG. 1). Field 304 indicates information related to criteria received from a user used to define the patient population. In this example, using field 304, a user may enter and/or select information related to target social determinants of health, the patient population, target chronic conditions, and target physician organizations. Field 302 indicates a number of patients in the patient population. Field 300 provides an indication of the relative influence of individual weighted features 311, 313, 315, 317, 319 on the distribution. Fields 306 and 308 illustrate health outcome risk indicators 312 (e.g., shown as circles in this example) and 314 (shown as a plurality of user expandable lists/icons in this example) for medical conditions in specific regions (e.g., zip codes and/or other postal codes) of the geographical area, and/or other information. FIG. 3 illustrates health outcome risk indicators 312 comprising shaded areas on a map of the geographic area. In FIG. 3, a size of a given shaded area indicates a population of a specific region to which the health outcome risk indicators apply. In some embodiments, as shown in FIG. 3, a color and/or a darkness of the given shaded area on the map of the geographic area indicates a medical condition to which the health outcome risk indicators apply. In some embodiments, as shown in FIG. 3, the display of the distribution of predicted health outcome information for a patient population in a geographical area includes one or more numerical indications 320 related to health outcome predictions for the geographical area (e.g., a social determinants of health index score and a list of the relative contributions 311-319 to that score from various features of the demographic, social, and prior health outcome information).

Figure 4:
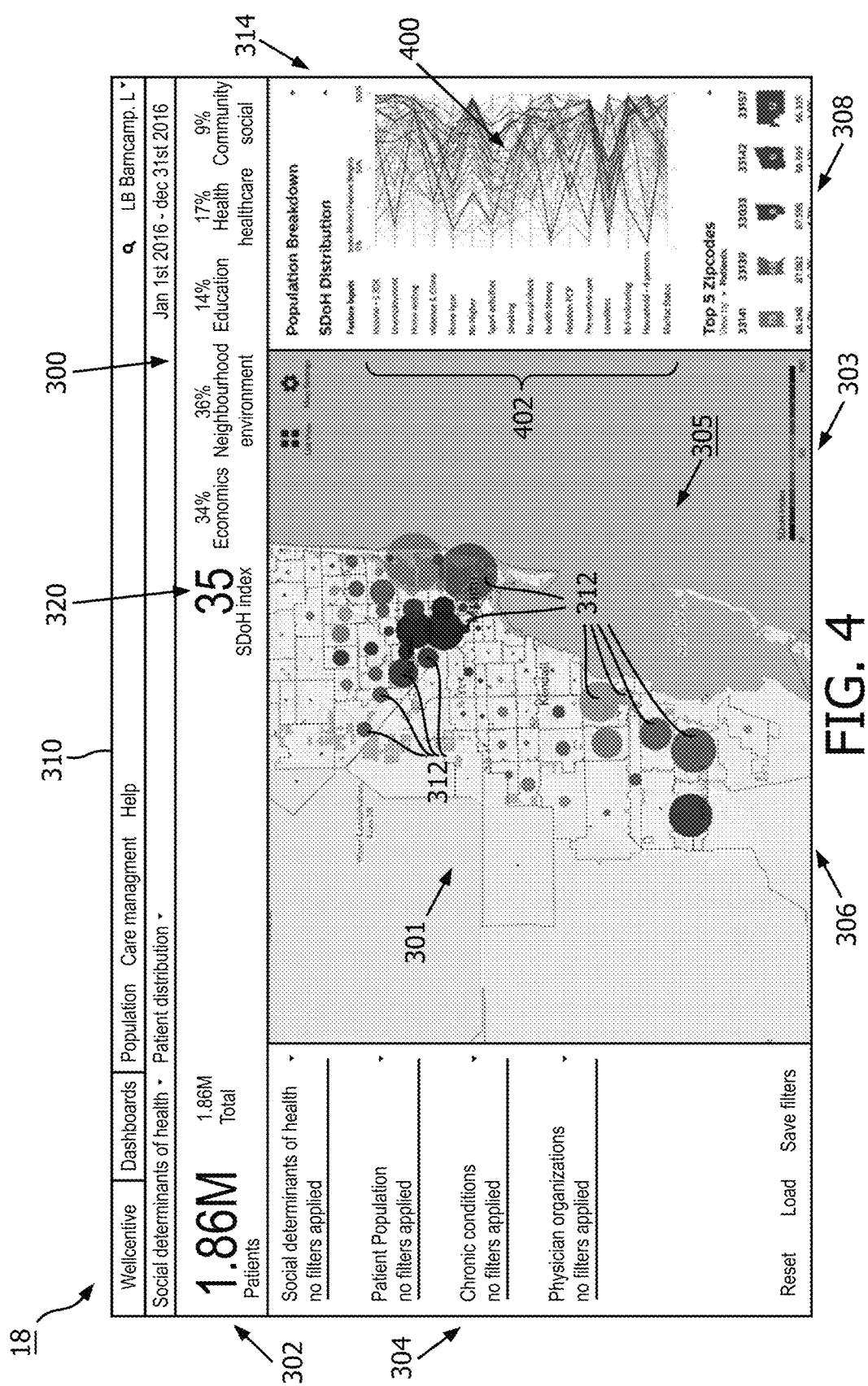
FIG. 4 illustrates the distribution of the predicted health outcome information for the patient population in the geographical area but with a portion of a health outcome risk indicator expanded to show lines indicating a relative influence of several social information features on the distribution, in accordance with one or more embodiments.

FIG. 4 also illustrates distribution 301 of predicted health outcome information 303 for a patient population in geographical area 305 (e.g., greater Miami). In FIG. 4, a portion of health outcome risk indicator 314 (shown as a plurality of user expandable lists/icons) has been expanded (e.g., by pointing and clicking, touching a touchscreen, hovering with a pointer, etc.) to show lines 400 indicating a relative influence of several social information features 402 on distribution 301 of predicted health outcome information 303. Individual lines 400 are associated with individual feature 402 inputs used to build the predictive model (described above). Lines 400 closer to the edge of view 310 indicate more influence on distribution 301. In the example shown in FIG. 4, lines 400 are shaded differently based on zip code. In this way, lines 400 illustrate which features 402 weigh more heavily (e.g., are more important) for a specific region (e.g., zip code) of a geographical area.

Figure 5:
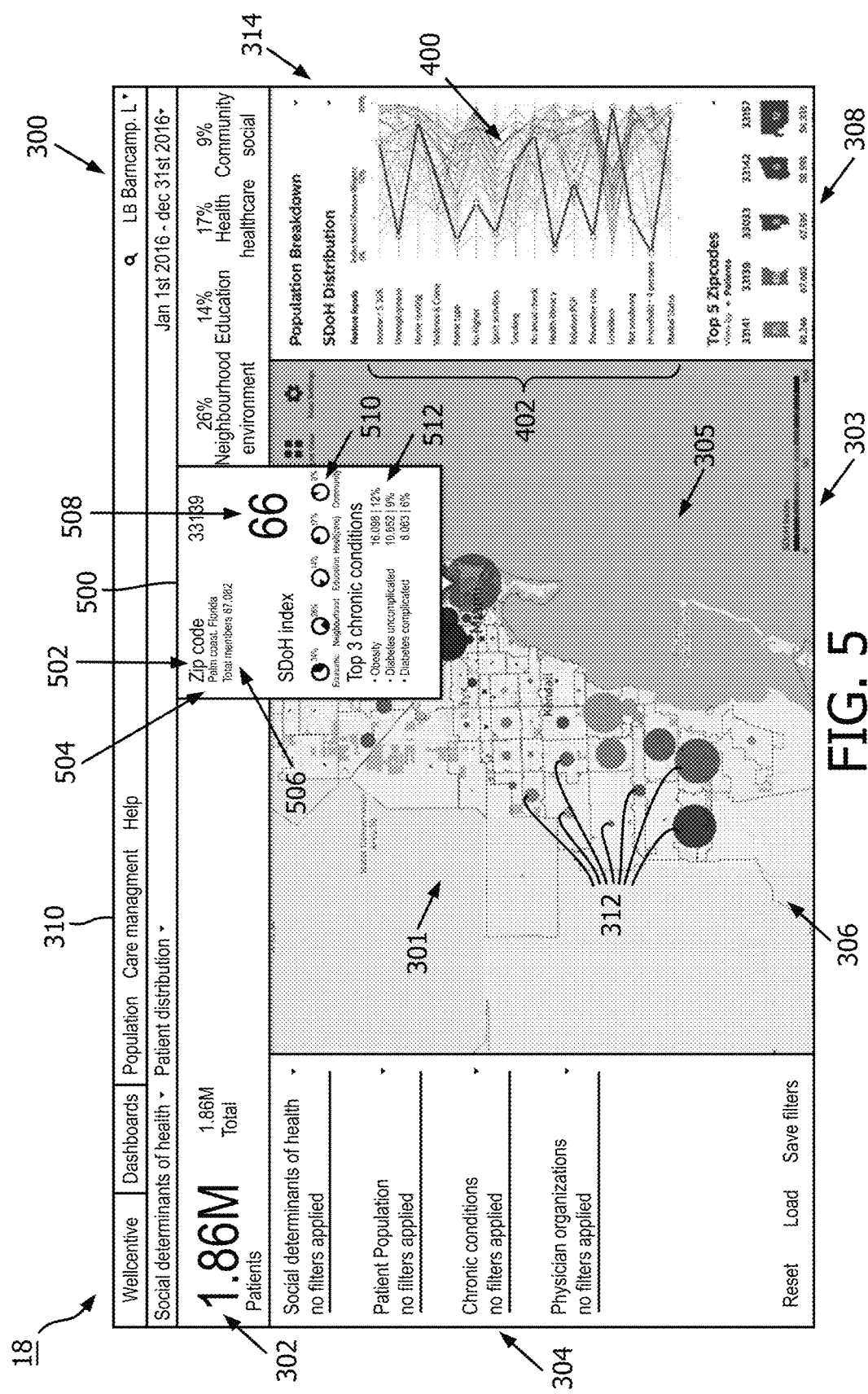
FIG. 5 illustrates how hovering over a specific region of a map of the geographical area causes display of additional information, in accordance with one or more embodiments.

FIG. 5 illustrates how hovering (in this example) over and/or other selection of a specific region (e.g., zip code) of geographical area 305 causes display of additional information. In FIG. 5, the additional information is displayed in a pop-up field 500 that corresponds to the specific region. Pop-up field 500 comprises an indication 502 of a postal (e.g., zip) code associated with the specific region, a name 504 of the specific region, and a total population and/or a total number of patients 506 in a medical provider system in the specific region. Pop-up field 500 comprises a numerical indication 508 related to health outcome predictions for the specific region (e.g., a social determinants of health index score that indicates an overall health of the region relative to other regions). Pop-up field 500 comprises graphical representations 510 of relative contributions of individual factors (e.g., features related to economics of the specific region, neighborhood characteristics, education, health of individual patients, and community interaction in this example) to numerical indication 508. Pop-up field 500 comprises a listing 512 of the most common chronic conditions for the specific region. These examples of the information displayed in pop-up field 500 are not intended to be limiting. In some embodiments, for example, the information displayed in pop-up field 500 may change based on the specific region and/or the geographical area, information entered and/or selected by a user 12 (FIG. 1) to adjust a prediction model and/or the modeled patient population (e.g., via field 304), and/or other factors. In some embodiments, display component 26 (FIG. 1) is configured such that the appearance (e.g., shape, location in view 310, a level of transparency, etc.) of pop-up field 500 is customizable by a user. In some embodiments, display component 26 is configured such that the information included in pop-up field 500 is customizable by a user 12. The appearance of pop-up field 500 and the information displayed in pop-up field 500 may be customizable via entries and/or selections made by the user 12 via computing device 16 and/or a graphical user interface 18, for example.

Figure 6:
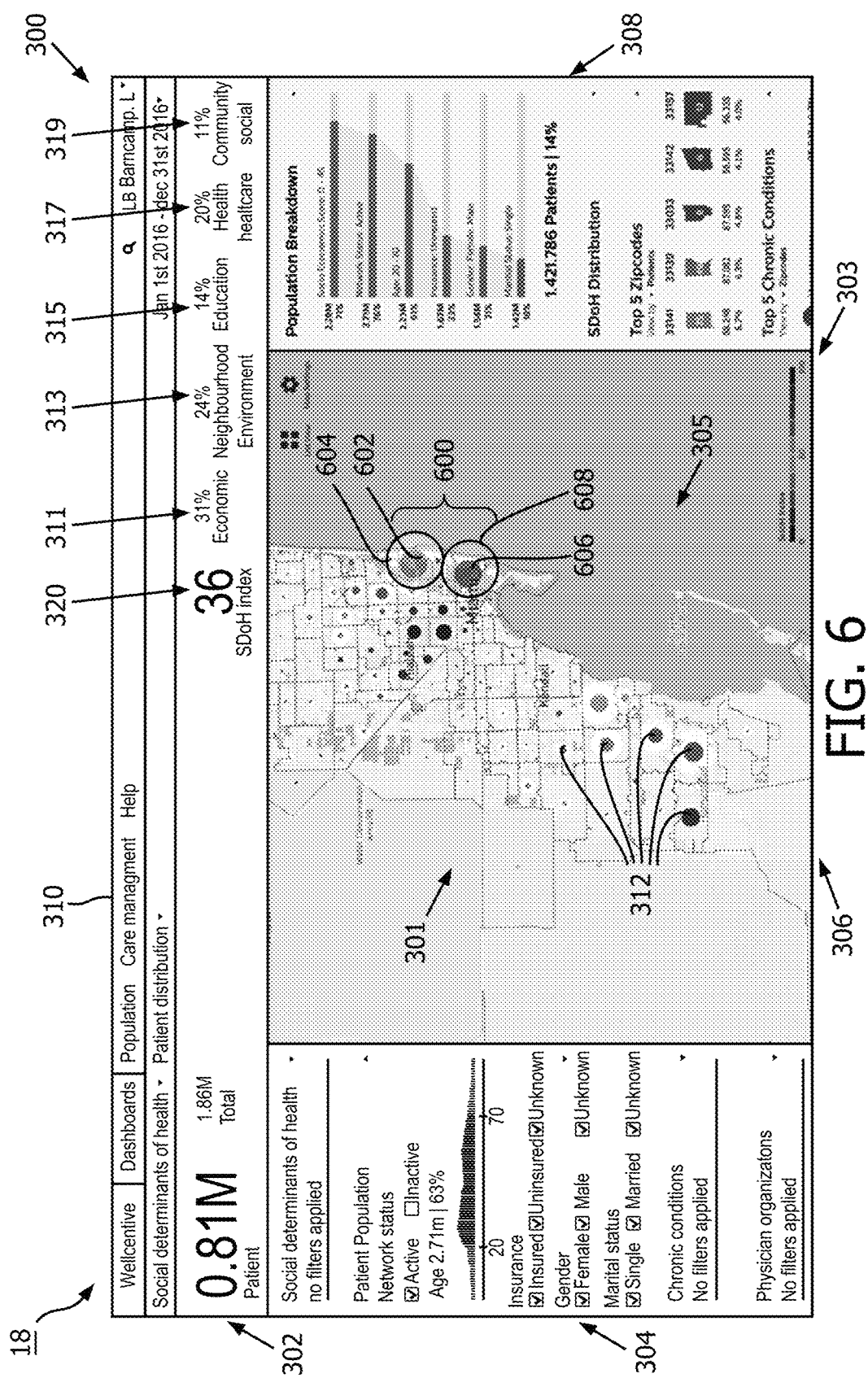
FIG. 6 illustrates a field of a display of the distribution that has been expanded to show a menu of selectable features of the patient population, a corresponding statistics breakdown for the population selected in the expanded field, and one or more risk indicators comprising concentric circles on a map of the geographic area where first larger concentric circles indicate total populations for specific regions, and second smaller concentric circles that indicate populations in the specific regions to which the selected health outcome risk indicators apply, in accordance with one or more embodiments.

FIG. 6 illustrates distribution 301 of predicted health outcome information 303 for the patient population in geographical area 305 (e.g., greater Miami). In FIG. 6, a patient population portion of field 304 (shown in previous figures as a user expandable list/icon) has been expanded (e.g., by pointing and clicking, touching a touchscreen, hovering with a pointer, etc.) to show a menu of selectable features of the patient population a user may check or uncheck (in this example) to define the patient population. Display component 26 (FIG. 1) is configured such that, responsive to a user making selections in field 304, field 308 displays corresponding statistics for the population breakdown selected in field 304. FIG. 6 also displays how health outcome risk indicators 312 may be customized by display component 26. In this example, one or more risk indicators 600 comprise concentric circles 602, 604, 606, and 608 on a map of geographic area 305. Concentric circles 604 and 608 indicate total populations for the specific regions (e.g., zip codes) that correspond to the circles, and smaller concentric circles 602 and 606 indicate populations in the specific regions to which the health outcome risk indicators apply. In the example in FIG. 6, the populations in the specific regions to which the health outcome risk indicators apply (e.g., represented by smaller concentric circles 602 and 606) are those that meet the criteria selected by a user via field 304, for example.

Figure 7:
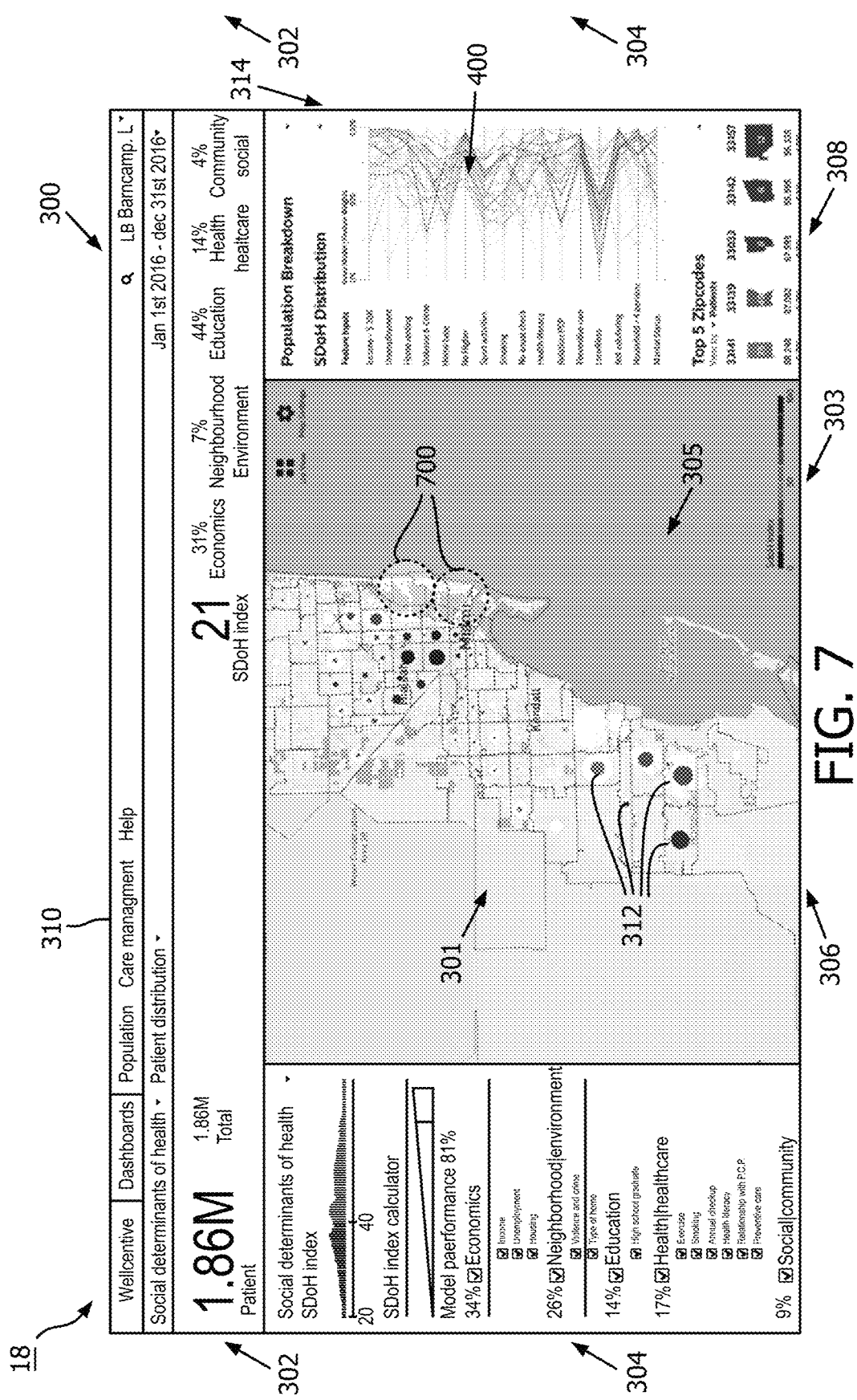
FIG. 7 illustrates a social determinants of health (e.g., social information features) portion of a field that has been expanded to show a menu of selectable social determinants of health of the patient population a user may use to filter the health outcome risk indicators displayed on the map and customize the output from one or more models generated by the model component, in accordance with one or more embodiments.

FIG. 7 illustrates distribution 301 of predicted health outcome information 303 for the patient population in geographical area 305 (e.g., greater Miami). In FIG. 7, a social determinants of health (e.g., social information features) portion of field 304 (shown in previous figures as a user expandable list/icon) has been expanded (e.g., by pointing and clicking, touching a touchscreen, hovering with a pointer, etc.) to show a menu of selectable social determinants of health (e.g., social information features) of the patient population a user may check or uncheck, move sliding indicators, etc. (in this example) to filter the health outcome risk indicators 312 displayed on map 305. In this example, dotted indicators 700 are no longer displayed because of the selections made by a user (e.g., user 12 shown in FIG. 1) via field 304. As shown in FIG. 7, a user may also customize the output from the one or more models described above (e.g., the way a social determinants of health index is computed) by selecting features to include in the model via field 304. Advantageously, this allows the user to view a specific population for which some features (e.g., de-selected by a user via field 304) may not be applicable.

Figure 8:
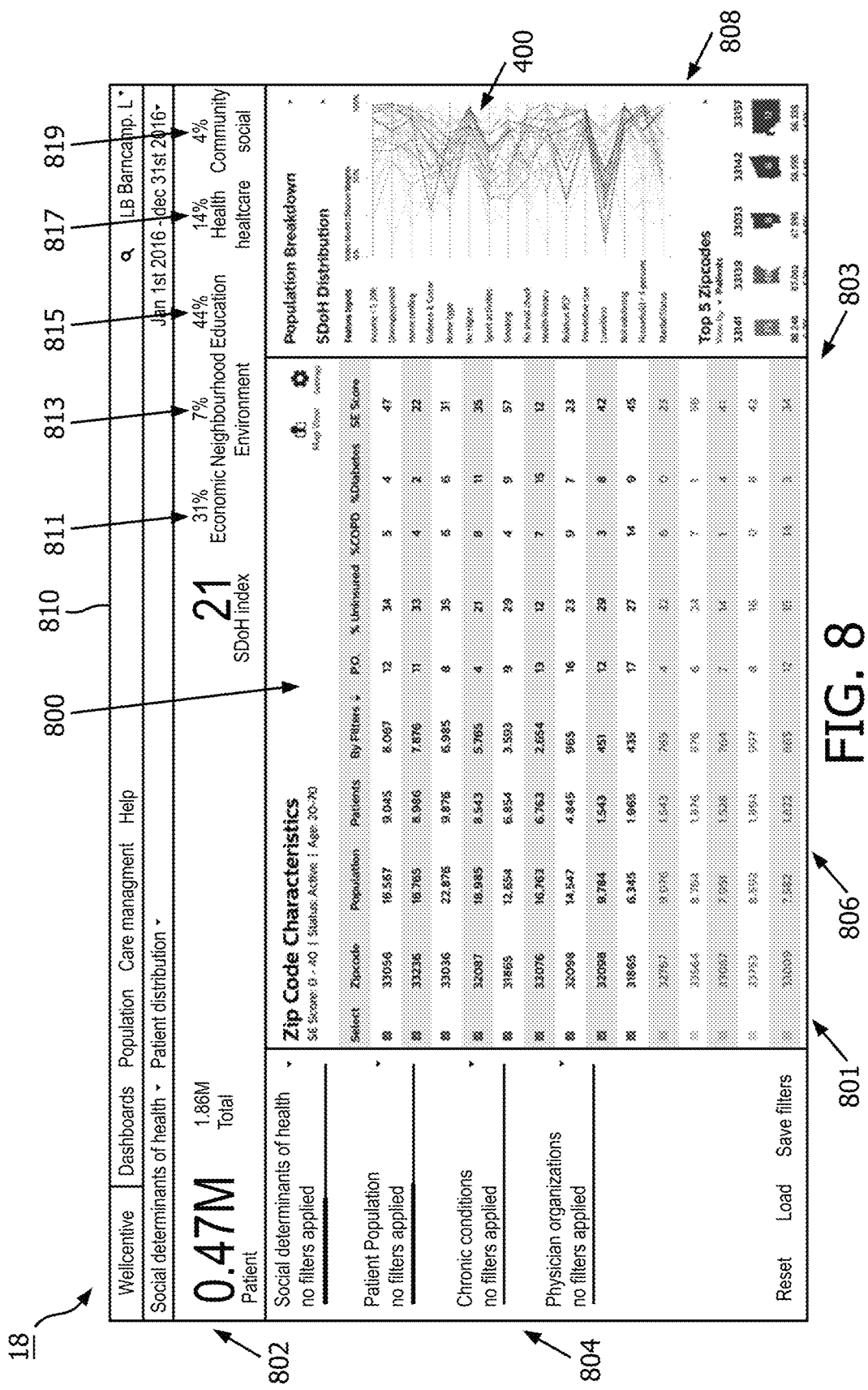
FIG. 8 illustrates a distribution of predicted health outcome information for a patient population in a geographical area, with an information table replacing a map of the geographical area, in accordance with one or more embodiments.

FIG. 8 illustrates a distribution 801 of predicted health outcome information 803 for a patient population in a geographical area, with an information table 800 replacing a map of the geographical area. FIG. 8 (like FIG. 3) illustrates a plurality of fields 800, 802, 804, 806, 808, in a view 810 of graphical user interface 18 (of computing devices 16 shown in FIG. 1). Field 804 indicates information related to criteria received from a user used to define the patient population. Field 802 indicates a number of patients in the patient population. Field 800 provides an indication of the relative influence of individual weighted features 811, 813, 815, 817, 819 on the distribution. Field 806 includes table 800. Table 800 comprises information about the patient population including postal (e.g., zip) codes, population, number of patients, and other demographic, social, and health outcome features.

Figure 9:
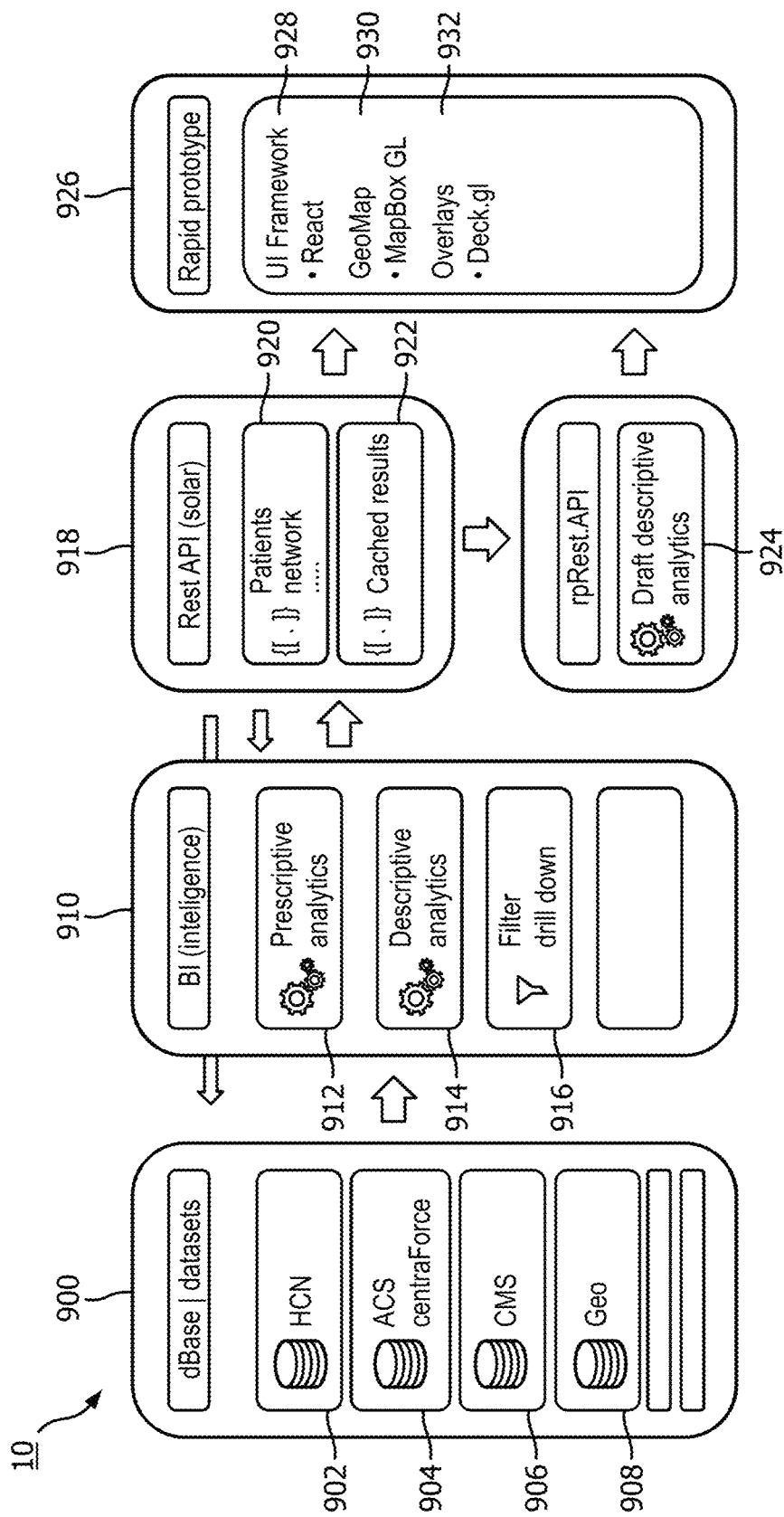
FIG. 9 illustrates an example of a possible front end framework for the system, in accordance with one or more embodiments.
Figure 10:
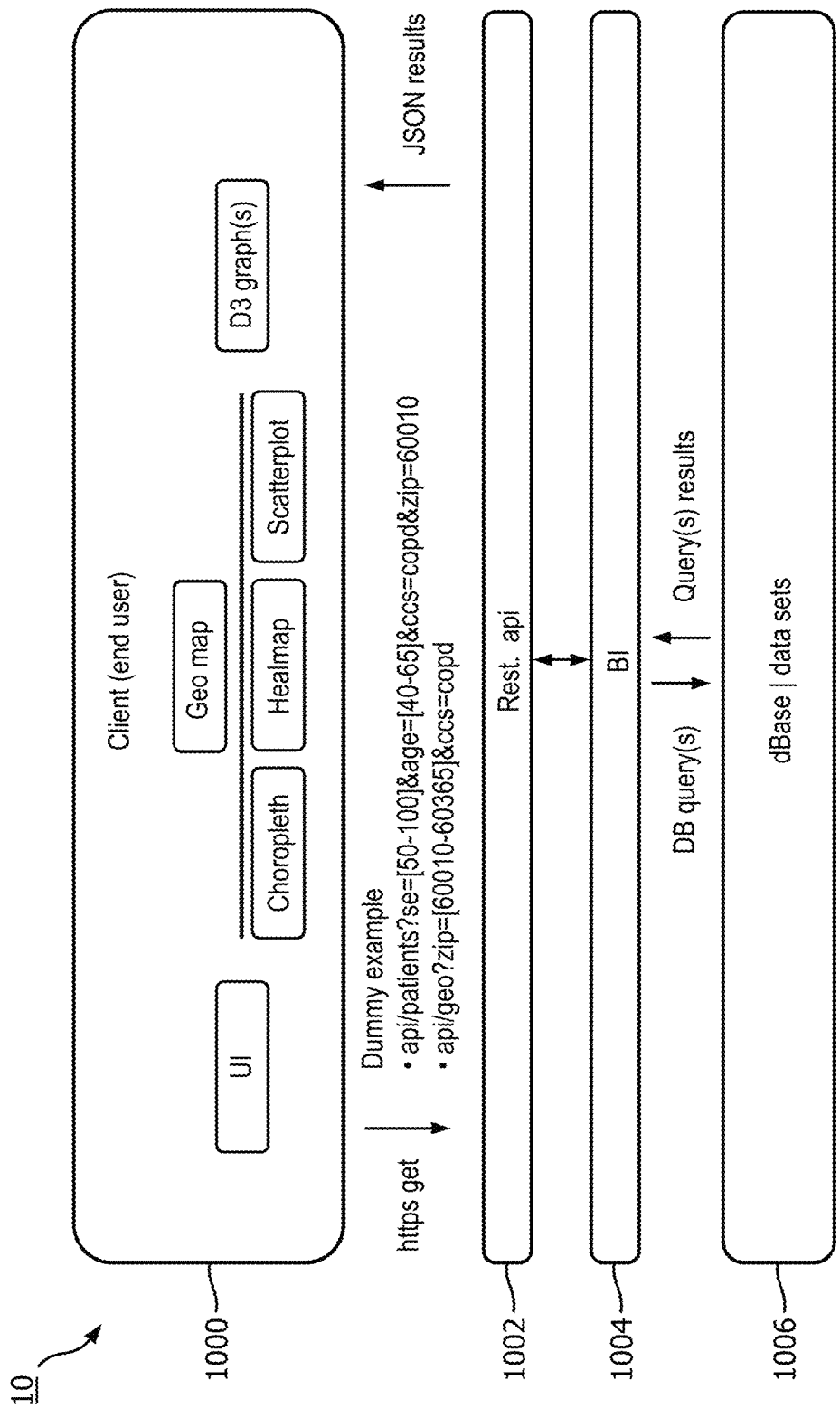
FIG. 10 illustrates a schematic example of possible communications between different components of the system, in accordance with one or more embodiments.

FIG. 9 and FIG. 10 illustrate an example of a possible front end framework (FIG. 9) and a schematic example of possible communications between different components of system 10 (FIG. 10). In some embodiments, system 10 may be a stand-alone web based tool, served by a Data Science Platform (DSP), with a Business Intelligence (BI) layer on the DSP, and with data access through a Rest application programming interface (API) (JSON) on the DSP. In some embodiments, the front end framework comprises and/or relies on React, MapBox GL, Deck.gl, data visualization and/or client side rendering tools, and/or other tools. FIG. 9 illustrates various databases 900 (including HCN 902, ACS/CentraForce 904, CMS 906, and Geo 908); a BI layer 910 (comprising prescriptive analytics 912, descriptive analytics 914, and filter/drill down 916); a Rest API 918 (comprising patients network 920, cached results 922, and (in some embodiments) draft descriptive analytics 924); and a rapid prototype layer 926 comprising UI Framework 928 (React), GeoMap 930 (MapBox GL), and Overlays 932 (Deck.gl). FIG. 10 illustrates communications between a client (e.g., an end user using a computing device 16 shown in FIG. 1) 1000, a Rest API 1002, a BI layer 1004, and databases 1006. As shown in FIG. 10, patient population criteria and/or other information (e.g., "https get") is communicated from client 1000 through Rest API 1002 to BI layer 1004. Databases 1006 are queried and return query results to BI layer 1004.

These results pass back through Rest API 1002 and on to client 1000 (e.g., "JSON Results") for display.

Returning to FIG. 1, electronic storage 30 comprises electronic storage media that electronically stores information (e.g., demographic information, social information, health outcome information, mathematical equations, models, prediction model and/or neural network inputs and/or outputs, etc.). The electronic storage media of electronic storage 30 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 30 may be (in whole or in part) a separate component within system 10, or electronic storage 30 may be provided (in whole or in part) integrally with one or more other components of system 10 (e.g., external resources 14, a computing device 16, processor 20, etc.). In some embodiments, electronic storage 30 may be located in a server together with processor 20, in a server that is part of external resources 14, and/or in other locations. Electronic storage 30 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 30 may store software algorithms, information determined by processor 20, information received by system 10 via computing devices 16, and/or other external computing systems, information received from external resources 14, and/or other information that enables system 10 to function as described herein.

Figure 11:
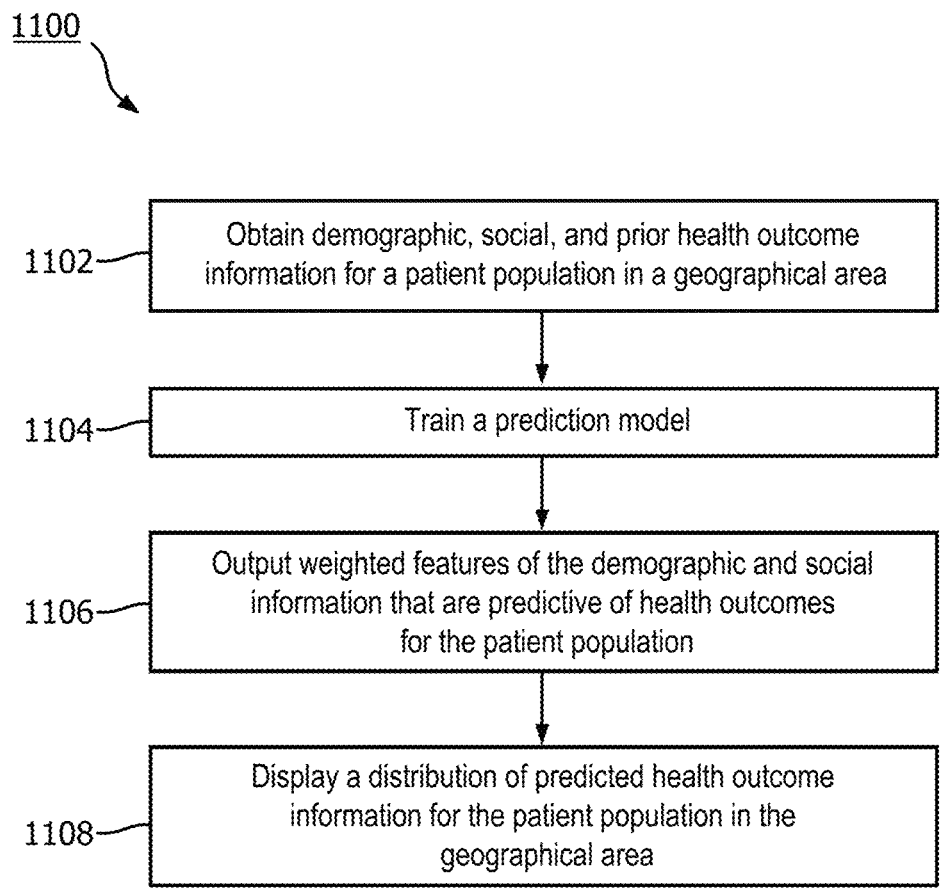
FIG. 11 illustrates a method for displaying distributions of predicted health outcome information for patient populations in geographical areas, in accordance with one or more embodiments.

FIG. 11 illustrates a method 1100 for displaying distributions of predicted health outcome information for patient populations in geographical areas by generating prediction models trained on demographic, social, and prior health outcome information of the patient populations with a display system. The system comprises one or more hardware processors and/or other components. The one or more hardware processors are configured by machine readable instructions to execute computer program components. The computer program components include an information component, a model component, a display component, and/or other components. The operations of method 1100 presented below are intended to be illustrative. In some embodiments, method 1100 may be accomplished with one or more additional operations not described, and/or without one or more of the operations discussed. Additionally, the order in which the operations of method 1100 are illustrated in FIG. 11 and described below is not intended to be limiting.

In some embodiments, method 1100 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1100 in response to instructions stored electronically on an electronic storage medium. The one or more processing devices may include one or more devices configured through hardware, firmware, and/or software to be specifically designed for execution of one or more of the operations of method 1100.

At an operation 1102, demographic, social, and prior health outcome information for a patient population in a geographical area are obtained. The demographic and social information are related to one or more of economics, neighborhood environments, education, health insurance coverage, or social interactions of the patient population. The prior health outcome information indicates one or more of medical conditions experienced by the patient population, treatments received by the patient population, or results of the treatments on the medical conditions for the patient population. In some embodiments, operation 1102 is performed by a processor component the same as or similar to information component 22 (shown in FIG. 1 and described herein).

At an operation 1104, a prediction model is trained. The prediction model is caused to be trained based on the demographic, social, and prior health outcome information, by providing the demographic, social, and prior health outcome information as input to the prediction model, and/or by other methods. In some embodiments, operation 1104 is performed by a processor component the same as or similar to model component 24 (shown in FIG. 1 and described herein).

At an operation 1106, the prediction model outputs weighted features of the demographic and social information that are predictive of health outcomes for the patient population. In some embodiments, operation 1106 is performed by a processor component the same as or similar to model component 24 (shown in FIG. 1 and described herein).

At an operation 1108, a distribution of predicted health outcome information for the patient population in the geographical area is displayed. The display is based on the weighted features and/or other information. The distribution of predicted health outcome information comprises one or more fields in one or more views of a graphical user interface indicating information related to one or more of: criteria received from a user used to define the patient population, a number of patients in the patient population, an indication of relative influence of individual weighted features on the distribution, or health outcome risk indicators for medical conditions in specific regions of the geographical area. In some embodiments, the specific regions of the geographical area correspond to postal codes that divide the geographical area into the specific regions. In some embodiments, the health outcome risk indicators comprise shaded areas on a map of the geographic area, with a size of a given shaded area indicating a population of a specific region to which the health outcome risk indicators apply. In some embodiments, a color of the given shaded area on the map of the geographic area indicates a medical condition to which the health outcome risk indicators apply. In some embodiments, the health outcome risk indicators comprise concentric circles on a map of the geographic area, with a first concentric circle indicating a total population for the specific region, and a second smaller concentric circle indicating a population to which the health outcome risk indicators apply. In some embodiments, operation 1108 is caused by a processor component the same as or similar to display component 26 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to display distributions of predicted health outcome information for patient populations in geographical areas by generating prediction models trained on demographic, social, and prior health outcome information of the patient populations, so that a medical care provider system can better geographically align resources based on the distributions of predicted health outcome information for the patient populations in the geographical areas compared to an existing alignment of the resources, the system comprising:

an electronic storage medium storing machine readable instructions configured to cause one or more hardware processors to:

obtain, by the one or more hardware processors, demographic, social, and prior health outcome information for a patient population in a geographical area, wherein the demographic and social information relates to one or more of economics, neighborhood environments, education, health insurance coverage, or social interactions of the patient population, wherein the prior health outcome information indicates one or more of medical conditions experienced by the patient population, treatments received by the patient population, or results of the treatments on the medical conditions for the patient population, and wherein the demographic, social, and prior health outcome information is, at least in part, sourced from one or more sensors, and wherein the one or more sensors are coupled to one or more wearable devices configured to track physiological characteristics;

train, by the one or more hardware processors, a prediction model comprising one or more neural networks based on the demographic, social, and prior health outcome information, wherein:

the one or more neural networks each comprise a collection of neural units, with each neural unit of a neural network connected with other neural units of the neural network, and with such connections being enforcing or inhibitory in their effect on an activation state of connected neural units, the neural network including multiple layers of neural units where a signal path traverses from front layers to back layers;

the demographic, social, and prior health outcome information is inputted to the prediction model to cause a relative influence of each feature of the demographic, social, and prior health outcome information relative to other features to be determined by the one or more one or more neural networks, and the demographic, social, and prior health outcome information is retrieved from a non-transitory computer readable storage medium;

output, by the one or more hardware processors, weighted features of the demographic and social information that are predictive of health outcomes for the patient population based on the relative influence of each feature from the prediction model; and display, by the one or more hardware processors, a distribution of predicted health outcome information for the patient population in the geographical area based on the weighted features, the displaying of the distribution of predicted health outcome information comprising simultaneous display of a plurality of fields and/or views of a graphical user interface indicating information related to:

criteria received from a user used to define the patient population, a number of patients in the patient population, an indication of relative influence of individual weighted features on the distribution, and health outcome risk indicators for medical conditions in specific regions of the geographical area.

2. The system of claim 1, wherein the specific regions of the geographical area correspond to postal codes that divide the geographical area into the specific regions.

3. The system of claim 1, wherein the one or more hardware processors are configured such that the display of the distribution of predicted health outcome information for the patient population in the geographical area includes the health outcome risk indicators for medical conditions in specific regions of the geographical area, and wherein the health outcome risk indicators comprise shaded areas on a map of the geographic area, wherein the shaded areas indicate a population of a specific region to which the health outcome risk indicators apply.

4. The system of claim 3, wherein the one or more hardware processors are configured such that a color of a given shaded area on the map of the geographic area indicates a medical condition to which the health outcome risk indicators apply.

5. The system of claim 3, wherein the one or more hardware processors are configured such that a darkness of a given shaded area on the map of the geographic area indicates a medical condition to which the health outcome risk indicators apply.

6. The system of claim 1, wherein the health outcome risk indicators comprise concentric circles on a map of the geographic area, with a first concentric circle indicating a total population for the specific region, and a second smaller concentric circle indicating a population to which the health outcome risk indicators apply.

7. A method for displaying distributions of predicted health outcome information for patient populations in geographical areas by generating prediction models trained on demographic, social, and prior health outcome information of the patient populations with a display system, so that a medical care provider system can geographically align resources based on the distributions of predicted health outcome information for the patient populations in the geographical areas compared to an existing alignment of the resources, the system comprising an electronic storage medium storing machine readable instructions configured to cause one or more hardware processors to perform steps of the method, the method comprising:

obtaining, by the one or more hardware processors, demographic, social, and prior health outcome information for a patient population in a geographical area, wherein the demographic and social information relates to one or more of economics, neighborhood environments, education, health insurance coverage, or social interactions of the patient population; wherein the prior health outcome information indicates one or more of medical conditions experienced by the patient population, treatments received by the patient population, or results of the treatments on the medical conditions for the patient population, wherein the demographic, social, and prior health outcome information is, at least in part, sourced from one or more sensors, and wherein the one or more sensors are coupled to one or more wearable devices configured to track physiological characteristics;

training, by the one or more hardware processors, a prediction model comprising one or more neural networks based on the demographic, social, and prior health outcome information, wherein:

the one or more neural networks each comprise a collection of neural units, with each neural unit of a neural network connected with other neural units of the neural network, and with such connections being enforcing or inhibitory in their effect on an activation state of connected neural units, the neural network including multiple layers of neural units where a signal path traverses from front layers to back layers;

the demographic, social, and prior health outcome information is inputted to the prediction model to cause a relative influence of each feature of the demographic, social, and prior health outcome information relative to other features to be determined by the one or more one or more neural networks, and the demographic, social, and prior health outcome information is retrieved from a non-transitory computer readable storage medium;

outputting, by the one or more hardware processors, weighted features of the demographic and social information that are predictive of health outcomes for the patient population based on the relative influence of each feature from the prediction model; and displaying, by the one or more hardware processors, a distribution of predicted health outcome information for the patient population in the geographical area based on the weighted features, the displaying of the distribution of predicted health outcome information comprising simultaneous display of a plurality of fields and/or views of a graphical user interface indicating information related to:

criteria received from a user used to define the patient population, a number of patients in the patient population, an indication of relative influence of individual weighted features on the distribution, and health outcome risk indicators for medical conditions in specific regions of the geographical area.

8. The method of claim 7, wherein the specific regions of the geographical area correspond to postal codes that divide the geographical area into the specific regions.

9. The method of claim 7, wherein the display of the distribution of predicted health outcome information for the patient population in the geographical area includes the health outcome risk indicators for medical conditions in specific regions of the geographical area, and wherein the health outcome risk indicators comprise shaded areas on a map of the geographic area, wherein the shaded areas indicate a population of a specific region to which the health outcome risk indicators apply.

10. The method of claim 9, wherein a color of a given shaded area on the map of the geographic area indicates a medical condition to which the health outcome risk indicators apply.

11. The method of claim 7, wherein the health outcome risk indicators comprise concentric circles on a map of the geographic area, with a first concentric circle indicating a total population for the specific region, and a second smaller concentric circle indicating a population to which the health outcome risk indicators apply.

* * * * *